United States Patent [19]

Schwender et al.

[11] 4,033,961
[45] July 5, 1977

[54] PYRIDO[2-1-b]QUINAZOLIN-ONES AND THEIR METHODS OF PREPARATION

[75] Inventors: Charles F. Schwender, Lebanon; Brooks R. Sunday, Hackettstown, both of N.J.

[73] Assignee: Warner-Lambert Company, Morris Plains, N.J.

[22] Filed: Oct. 7, 1975

[21] Appl. No.: 620,471

[52] U.S. Cl. .................. 260/251 A; 260/256.4 F; 260/256.5 R; 424/251
[51] Int. Cl.² .......................................... C07D 239/88
[58] Field of Search ................ 260/251 A, 256.4 F

[56] References Cited

OTHER PUBLICATIONS

"Beilstein's Handbuch der Org Chemie", Band XXV, 2nd supplement, Sgst No. 3696, J. Springer, Berlin, (1954), p. 238.
Spath et al., Chem. Abstracts, vol. 32, col. 9089, 1938.

*Primary Examiner*—Donald G. Daus
*Assistant Examiner*—D. B. Springer
*Attorney, Agent, or Firm*—Albert H. Graddis; Frank S. Chow; George M. Yahwak

[57] ABSTRACT

This invention relates to novel compounds of the pyrido-[2,1-b]-quinazolin-one series and their methods of preparation. These compounds have utility as antiallergy agents.

7 Claims, No Drawings

PYRIDO[2-1-b]QUINAZOLIN-ONES AND THEIR METHODS OF PREPARATION

The present invention relates to the following generic series:

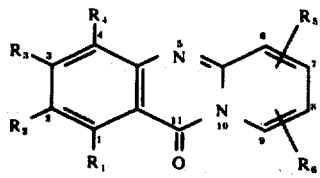

where $R_1$-$R_4$ is selected from the group consisting of hydrogen, halogen, cyano, alkoxy, alkyl, alkenyl, aminoalkoxy, hydroxyalkoxy, hydroxy, aralkyloxy, trifluoromethyl, nitro, amino, monoalkylamino, dialkylamino, aralkylamino, acylamino, sulfonylamino, carboxy, carboalkoxy, carboxamido or N-substitued carboxamido, methylsulfinyl, methylsulfonyl, arylsulfinyl, arylsulfonyl, sulfonamido, sulfonic acid, acrylic acid, oxyacetic acid, tetrazolyl, N-(tetrazolyl)-carboxamido and tetrazolylethylene, or mixture thereof. $R_5$ is selected from a group consisting of hydrogen, hydroxy, hydroxyalkyl, hydroxyalkoxy, carboxy, carboalkoxy, carboxamido and N-substitued carboxamido, tetrazolyl, N-tetrazolyl-carboxamido, tetrazolylethylene, sulfonamido and sulfonic acid, acrylic acid, cyano, oxyacetic acid and oxymethyltetrazolyl optionally appearing at positions 6-9 of the pyrido ring. $R_6$ is selected from a group consisting of hydrogen, hydroxyl, alkoxy and alkyl groups.

Those structural species which contain at least one acidic function (such as carboxyl, sulfonic and tetrazolyl, etc.) cyano or their esters or pharmaceutically acceptable salts, either at $R_5$ and/or at $R_1$ - $R_4$ are preferred. That is, if $R_1$ -$R_4$ is an acid group or ester, then $R_5$ may be as indicated above. If $R_5$ is an acidic group or ester, then $R_1$ -$R_4$ may be as indicated above. In addition, $R_5$ and $R_1$ -$R_4$ may both be acidic groups or their esters.

One analog, ($R_1$-$R_4$= H, $R_5$= 6-COOH and $R_6$= H), is known and is specifically excluded from the scope of this invention. This known compound possesses anti-inflammatory action. [See Netherlands Patent No. 6,414,717, granted 6/21/65]. Biological data has been provided in table I to show that this known isomer (799) is less active than those isomers of the invention.

Pharmaceutically acceptable salts of acids and bases are also included in the scope of this invention.

As used above, the term halogen refers to chlorine, bromine, and fluorine; alkoxy refers to radicals wherein the alkyl moiety contains one to eight carbon atoms, preferably 1 to 6 in straight or branched chains or as cyclic 4,5 carbons; alkyl refers to radicals containing one to eight carbon atoms, preferably 1 to 6 carbons in straight or branched chains or as cyclic 5 or 6 carbons; alkenyl refers to radicals of 1 to 6 carbons; aralkyl refers to benzyl, phenylethyl, and phenylpropyl radicals; aralkyloxy refers to the structures as defined for aralkyl; acyl relates to those radicals which are derived from alkanoic acids of 1 to 6 carbons, or aroyls such as benzoyl; sulfonyl refers to methylsulfonyl, phenylsulfonyl, or substituted-phenylsulfonyl.

The preferred compounds of this invention include:

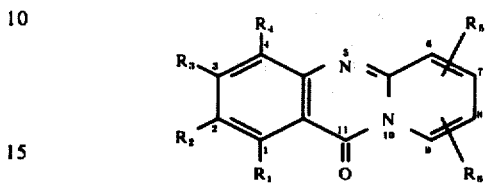

where:
1. $R_1$-$R_4$, $R_6$ = H, $R_5$ = 7-COOH
2. $R_1$-$R_4$, $R_6$ = H, $R_5$ = 8-COOH
3. $R_1$&$R_4$, $R_6$ = H, $R_2R_3$ = OCH$_3$, $R_5$ - 7-COOH
4. $R_1$&$R_4$, $R_6$ = H, $R_2R_3$ = OCH$_3$, $R_5$ = 8-COOH
5. $R_1$&$R_4$, $R_6$ = H, $R_2R_3$ = CH$_3$, $R_5$ = 7-COOH
6. $R_1$&$R_4$, $R_6$ = H, $R_2R_3$ = CH$_3$, $R_5$ = 8-COOH
7. $R_1$&$R_4$, $R_6$ = H, $R_2R_3$ = methylenedioxy, $R_5$ - 7-COOH
8. $R_1$&$R_4$, $R_6$ = H, $R_2R_3$ = methylenedioxy, $R_5$ = 8-COOH
9. $R_1$-$R_4$, $R_6$ = H, $R_5$ = 7-(tetraxolyl)
10. $R_1$-$R_4$, $R_6$ = H, $R_5$ = 8-(tetraxolyl)
11. $R_1$&$R_4$, $R_6$ = H, $R_{2R3}$ = OCH$_3$, $R_5$ = 7-(tetrazolyl)
12. $R_1$&$R_4$, $R_6$ = H, $R_2R_3$ = OCH$_3$, $R_5$ = 8-(tetrazolyl)
13. $R_1R_4R_6$ = H, $R_2R_3$ = CH$_3$, $R_5$ = 7-(tetrazolyl)
14. $R_1R_4R_6$ = H, $R_2R_3$ = CH$_3$, $R_5$ = 8-(tetrazolyl)
15. $R_1R_4R_6$ = H, $R_2R_3$ = methylenedioxy, $R_5$ = 7-(tetrazolyl)
16. $R_1R_4R_6$ = H, $R_2R_3$ = methylenedioxy, $R_5$ = 8-(tetrazolyl)
17. $R_1R_2R_4$, $R_6$ = H, $R_3$ = COOH, $R_5$ = 8-COOH
18. $R_1R_3R_4R_6$ = H, $R_2$ = COOH, $R_5$ = 8-COOH
19. $R_1R_2R_4R_6$ = H, $R_3$ = COOH, $R_5$ - 7-COOH
20. $R_1R_3R_4R_6$ = H, $R_2$ = COOH, $R_5$ = 7-COOH The compounds of this invention may be prepared by these chemical routes:

1. A fusion of the appropriately substituted-anthranilate ester with 1-1,25 equivalents of 2-chloropyridine-3,4,5- or 6-carboxylic acid and 0.05-1.1 equivalents of potassium iodide at 100-250° for 0.5–3 hours gives the crude product as a solid upon cooling. Purification is achieved by recrystallization or by washing the crude solid with a hot alcohol.

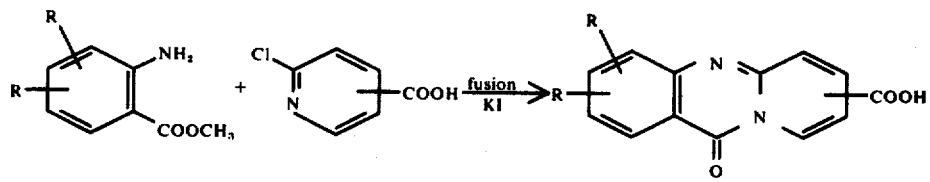

2. The appropriately substituted-anthranilic acid or ester is heated at reflux for 2–72 hours with 1–2 equivalents of the appropriate 2-chloro-pyridine in 5–20 parts glacial acetic acid or similar alkanoic acid. The expected product is obtained as a precipitate by cooling or by pouring the reaction mixture upon ice. The crude product is purified by recrystallization from pyridine or by washing with a hot alcohol, such as ethanol.

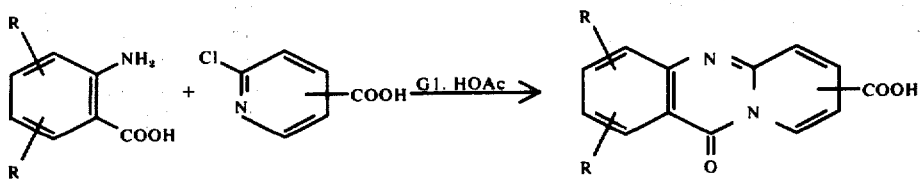

3. The desired products may also be obtained by heating, at relux temperature, 65°–140°, a mixture of the appropriately substituted-anthranilic acid or ester and 1–2 equivalents of 2-chloropyridine-3,4,5- or 6-carboxylic acid in 5–50 parts of an alcohol containing 0.1–1.1 equivalents of hydrochloric acid. The crude product is obtained as a precipitate from the reaction mixture and is purified by recrystallization or by washing with a hot alcohol, such as ethanol.

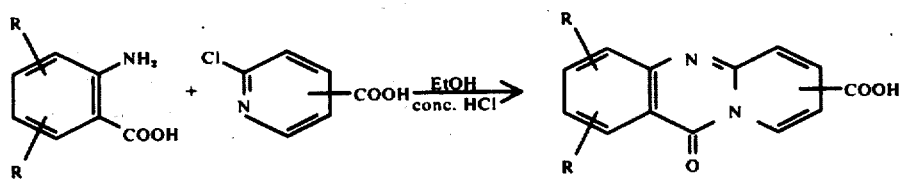

Furthermore, the chloronicotinic acids may be replaced in this reaction by the following pyridine analogs and any such combinations of $R_1$ and $R_2$:

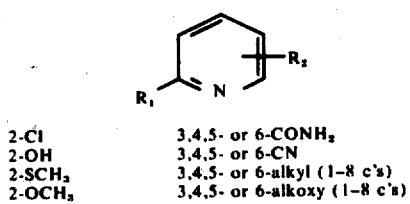

| | |
|---|---|
| 2-Cl | 3,4,5- or 6-CONH$_2$ |
| 2-OH | 3,4,5- or 6-CN |
| 2-SCH$_3$ | 3,4,5- or 6-alkyl (1–8 c's) |
| 2-OCH$_3$ | 3,4,5- or 6-alkoxy (1–8 c's) |

The following examples are given to more specifically define the method of making the preferred compounds of the formula:

EXAMPLE 1

11-oxo-11H-pyrido[2,1-b]quinazoline8-carboxylic acid

A reaction mixture containing 4.35g (31.8 mmol) of anthranilic acid, 5.00g (31.8 mmol) of 6-chloronicotinic acid, 3ml of conc. HCl and 80ml of ethanol was heated at reflux for 21 hours. The mixture was cooled and filtered to give 3.40g (38.9%) of the expected product, mp. 323°–325° dec. The analytical sample was obtained by recrystallization from methanol-ether, mp. 323°–325° dec.

Anal. Calcd. for $C_{13}H_8N_2O_3 \cdot HCl$: C, 56.44; H, 3.28; N, 10.13; Cl, 12.81. Found: C, 56.40; H, 3.30; N, 9.89; Cl, 12.68, 12.76.

EXAMPLE 2

3-carboethoxy-11-oxo-11H-pyrido[2,1-b]quinazoline-8-carboxylic acid

A mixture of 2.00g (11.1 mmol) of 2-aminoterephthalic acid, 1.73g (11.1 mmol) of 6-chloronicotinic acid, 2.5ml of conc. HCl and 25ml of ethanol was heated at reflux for 67 hours. The mixture was cooled and filtered to give 0.90g of solid, mp. 275°–324°. The crude material was recrystallized from 1-propanol and gave 0.40g of the mono-esterified product, mp. 283°–293° dec.

EXAMPLES

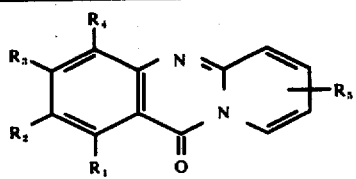

| Example | R$_1$ | R$_2$ | R$_3$ | R$_4$ | R$_5$ | mp |
|---|---|---|---|---|---|---|
| 799 | H | H | H | H | 6-COOH | 221.5–23° |
| 1 | H | H | H | H | 8-COOH | 323–25° dec. |
| 2 | H | H | COOC$_2$H$_5$ | H | 8-COOH | 290–293° dec. |
| 3 | H | —OCH$_2$O— | | H | 6-COOH | 300–304° dec. |
| | H | H | COOH | H | 8-COOH | 252° soften, 319° dec. |
| 503 | H | H | H | H | 8-CONH$_2$ | 338–44° dec. |
| 558 | H | CH$_3$ | H | H | 8-COOH | 328–33° dec. |
| 559 | H | Cl | H | H | 8-COOH | 347–348.5° dec. |
| 560 | H | OH | H | H | 8-COOH | 375–78° dec. |
| 561 | H | OCH$_3$ | H | H | 8-COOH | 327.5–330.5° dec. |
| 574 | H | H | CH$_3$ | H | 8-COOH | 307–309.5° dec. |
| 591 | H | H | Cl | H | 8-COOH | 330–36° dec. |
| | H | H | H | H | 7-CH$_3$ | 318–20° dec. |

Anal. Calcd. for $C_{16}H_{12}N_2O_5$: C, 61.54; H, 3.87; N, 8.97. Found: C, 61.55; H, 4.14; N, 8.86.

EXAMPLE 3

2,3-methylenedioxy-11-oxo-11H-pyrido[2,1-b]quinazoline-6-carboxylic acid

A mixture of 2.00g (10.4 mmol) of methyl 2-amino-4,5-methylenedioxybenzoate, 1067g (10.4 mmol) of 2-chloronicotinic acid and 50mg of KI was heated at 170° for 1 hour. The fusion or melt gradually solidified to an orange cake. The solid material was heated in boiling methanol (250 ml) and then filtered to yield 1.60g of crude product, mp. 273°–280° dec. The analytical sample was obtained by recrystallization from DMF, mp. 300°–304° dec.

Anal. Calcd. for $C_{14}H_8N_2O_5$: C, 59.16; H, 2.84; N, 9.86. Found: C, 59.12; H, 3.00; N, 10.01.

Compounds of this series offer the advantage of oral activity when compared with the reference standard, intal (Fisons). In addition, analogs in this series offer enhanced potency compared with intal (chromoglycate di sodium) and 799, as can be seen in Table I.

H. C. Mansmann, Eds., John Wiley and Son, N.Y., 1975], these compounds as shown in Table I may be administered orally, parenterally, or by aerosol at a dose of 0.005–20mg/kg. Compounds of this invention are useful in the management of allergic reactions such as bronchial asthma.

As seen, the Example 1 compound is active when given orally or intravenously whereas the closest analog is not. Furthermore, whereas the commerical compound is unactive when given intraperitonially and orally, the compounds of this invention are active for all three routes of administration.

We claim:
1. 7-cyano-11-oxo-11H-pyrido[2,1-b]quinazoline.
2. 7-methyl-11-oxo-11H-pyrido[2,1-b]quinazoline.
3. 3-(ethoxycarbonyl)-11-oxo-11H-pyrido[2,1-b]quinazoline-8-carboxylic acid.
4. 11-oxo-11H-1,3-dioxolo[4,5-g]pyrido[2,1-b]quinazoline-6-carboxylic acid.
5. 2-methyl-11-oxo-11H-pyrido[2,1-b]quinazoline-8-carboxylic acid.
6. 2-hydroxy-11-oxo-11H-pyrido[2,1-b]quinazoline-8-carboxylic acid.
7. 2-methoxy-11-oxo-11H-pyrido[2,1-b]quinazoline-8-carboxylic acid.

TABLE I

| Pyrido 2,1-b quinazolone Series | $ED_{50}$-PCA (rat) | | |
|---|---|---|---|
| | ip. | iv. | po. |
| Example 1 | 2.0mg/kg | 0.2mg/kg | 2.0mg/kg |
| 799 | 10mg/kg only 21% inhibition | — | 10mg/kg inactive |
| Intal* (Fisons) | inact. | 1–2mg/kg | inactive |

Compounds of this invention have been found to reduce allergic responses to antigen challenge by inhibiting antibody-antigen reactions in mammals such as rats. When tested in accordance with the procedure of Herzig [Immunopharmacology, M. E. Rosenthale and